(12) United States Patent
Nilforushan et al.

(10) Patent No.: US 7,739,748 B2
(45) Date of Patent: Jun. 22, 2010

(54) TEMPERATURE ALTERING GARMENT AND METHODS OF USE THEREON

(75) Inventors: Ali Nilforushan, Cardiff-by-the-Sea, CA (US); Kevin Bello, Escondido, CA (US)

(73) Assignee: SnapBac, LLC, Cardiff-by-the-Sea ( * ) Notice: Subject to any disclaimer, the term of this patent is extended or adjusted under 35 U.S.C. 154(b) by 281 days.

(21) Appl. No.: 11/838,776

(22) Filed: Aug. 14, 2007

(65) Prior Publication Data

US 2008/0201818 A1      Aug. 28, 2008

Related U.S. Application Data

(63) Continuation-in-part of application No. 11/804,552, filed on May 18, 2007.

(60) Provisional application No. 60/838,666, filed on Aug. 17, 2006.

(51) Int. Cl.
    *A41D 13/00*     (2006.01)
(52) U.S. Cl. ............... 2/69; 2/267; 2/268; 2/97; 2/462
(58) Field of Classification Search .............. 2/69, 2/2.94, 267, 268, 97, 102, 88, 462, 463; 450/36, 450/54–58; 5/413 R, 420
See application file for complete search history.

(56) References Cited

U.S. PATENT DOCUMENTS

| | | | |
|---|---|---|---|
| 233,275 A | 10/1880 | Osborn | |
| 541,536 A | 6/1895 | Hand | |
| 965,834 A | 7/1910 | Palmer | |
| 4,625,729 A | 12/1986 | Roney | |
| 4,985,924 A | 1/1991 | Matsuura | |
| 5,038,779 A | 8/1991 | Barry et al. | |
| 5,086,629 A | 2/1992 | Dibrell | |
| 5,146,625 A | 9/1992 | Steele et al. | |
| 5,187,814 A | 2/1993 | Gold | |
| 5,271,211 A | 12/1993 | Newman | |
| 5,302,806 A * | 4/1994 | Simmons et al. | ............ 219/211 |
| 5,537,954 A | 7/1996 | Beeghly | |

(Continued)

FOREIGN PATENT DOCUMENTS

CA           1261908           9/1989

(Continued)

*Primary Examiner*—Gary L Welch
*Assistant Examiner*—Alissa J Tompkins
(74) *Attorney, Agent, or Firm*—Fish & Associates, PC

(57) ABSTRACT

Human clothing has inner and outer flexible layers that define a space sufficiently large to position a thermal transfer element in any of multiple, non-overlapping positions. The space and the thermal transfer element preferably have cooperating sides of a hook-and-loop attachment. All suitable items of clothing are contemplated, but especially a shirt, jacket or pants that appear to others as a substantially normal garment. Each space has one or more openings, in either the inner or outer layers, and preferably at the shoulders or sides of the torso, or at the pocket areas of pants. The spaces are preferably large, not only relative to the size of a corresponding thermal transfer element, but also to the size of the garment. Thermal transfer elements are preferably disposed in pouches having a thermal insulation on that side, and have only a very thin, thermally transmissive, fabric on the other side.

19 Claims, 13 Drawing Sheets

U.S. PATENT DOCUMENTS

| | | |
|---|---|---|
| 5,826,273 A | 10/1998 | Eckes |
| 5,887,437 A | 3/1999 | Maxim |
| 6,432,125 B2 | 8/2002 | Kohout |
| 6,443,101 B1 | 9/2002 | Fazio |
| 7,065,983 B2 | 6/2006 | Trinh et al. |
| 2003/0061790 A1* | 4/2003 | Longtin ................. 54/79.2 |
| 2005/0154336 A1 | 7/2005 | Kloecker et al. |
| 2006/0213156 A1 | 9/2006 | Nilfuroshan |
| 2006/0218692 A1 | 10/2006 | Lamarque |

FOREIGN PATENT DOCUMENTS

| | | |
|---|---|---|
| DE | 20021260 | 4/2001 |

* cited by examiner

FIG.5
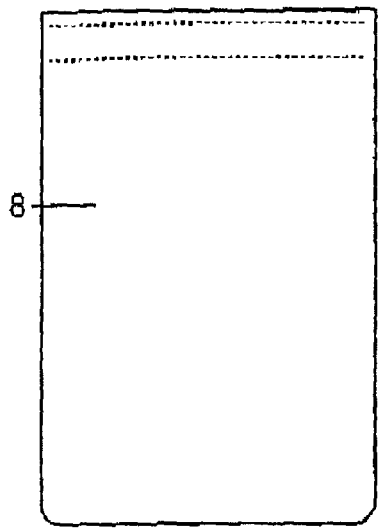
FIG.6
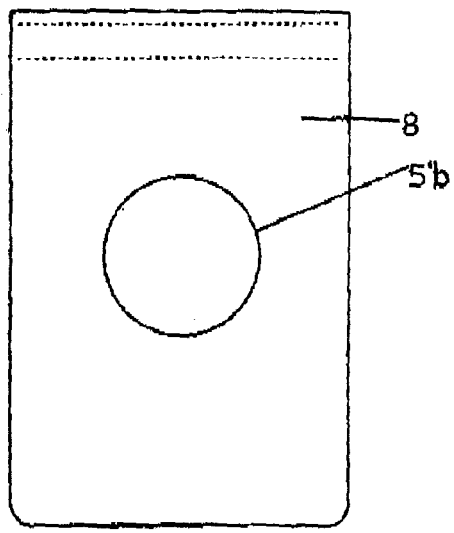
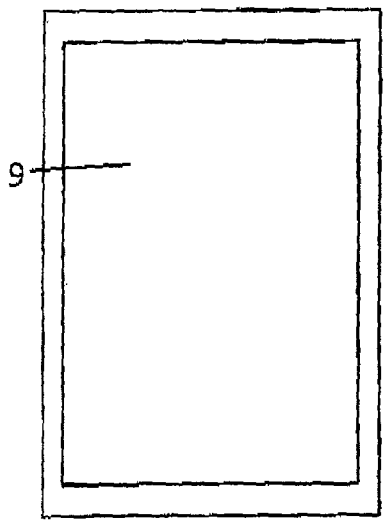
FIG.7
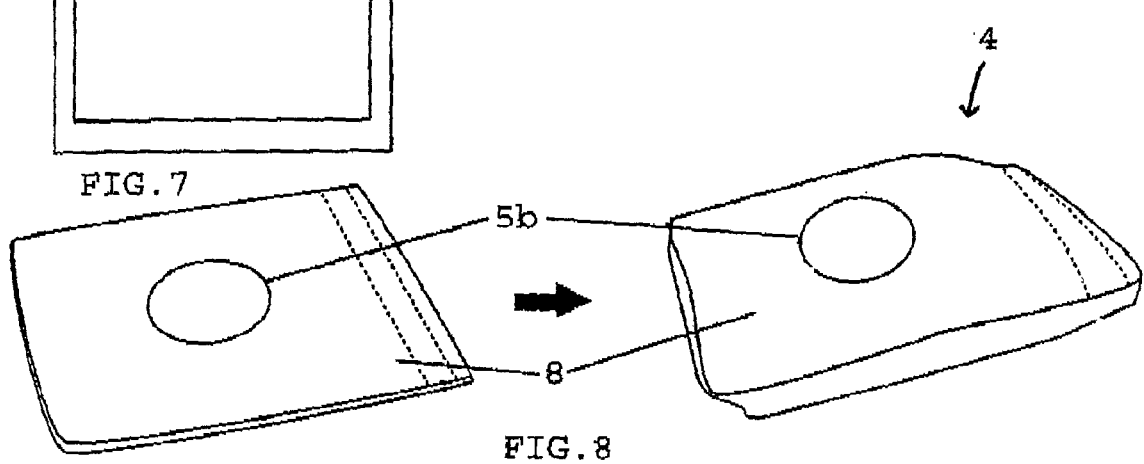
FIG.8

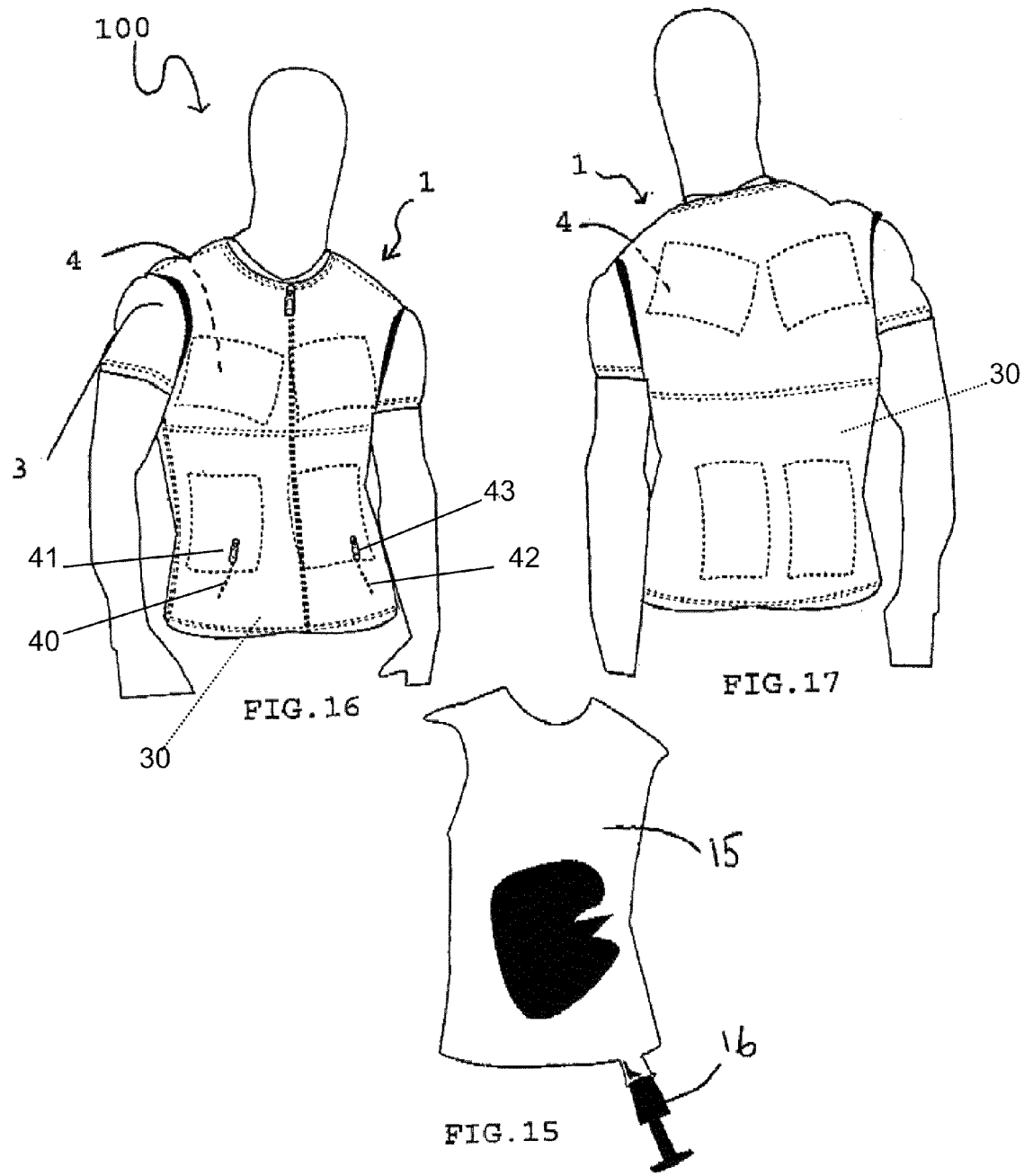

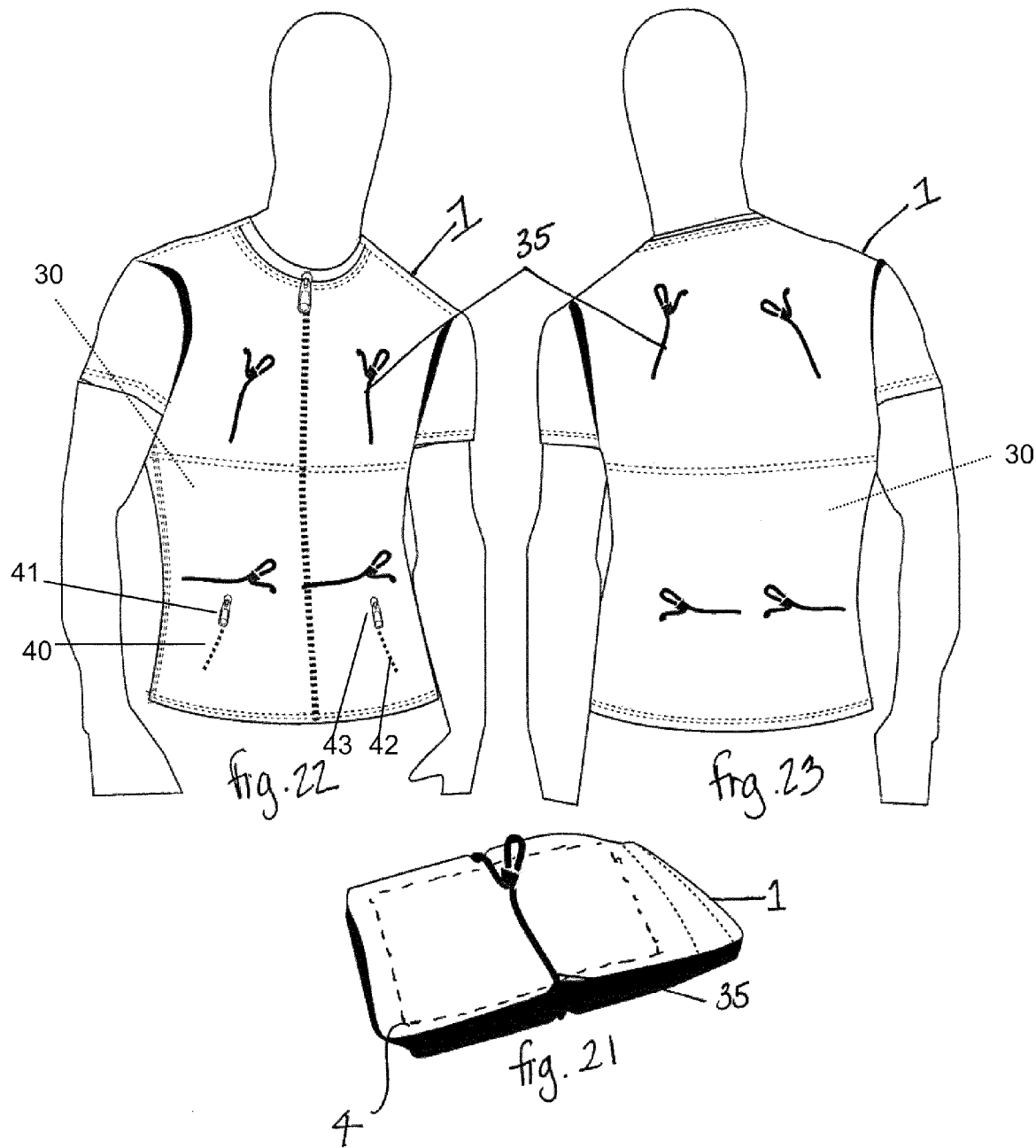

TEMPERATURE ALTERING GARMENT AND METHODS OF USE THEREON

CROSS-REFERENCE TO RELATED APPLICATION

This application is a CIP of U.S. application Ser. No. 11/804,552 filed May 18, 2007, which claims priority to U.S. provisional application No. 60/838,666 filed Aug. 17, 2006 and also claims priority to application Ser. No. 10/559,860 filed Dec. 6, 2005, which is a US national phase of International application no. PCT/US04/031540 filed Sep. 27, 2004, which claims priority to U.S. application Ser. No. 10/807,695 filed Mar. 24, 2004.

FIELD OF THE INVENTION

The field of the invention is clothing that accommodates heating and cooling pads.

BACKGROUND

It is known to heat or cool parts of the human body to prevent or treat injuries, relieve pain, improve flexibility, warm a person in a cold environment, cool a person in a hot environment, and so forth. A common method for heating or cooling a body part is to contact the part with a hot or cold pack, generically referred herein as a thermal transfer element.

There are many well known methods for applying thermal transfer elements to human body parts. One method is to manually hold a thermal transfer element in contact with a body part that is intended to be heated or cooled. This method has significant disadvantages. First, a person must engage the assistance of another in order to apply a thermal transfer element to a hard-to-reach area. Additionally, a person cannot alone simultaneously apply thermal transfer elements to more than a few areas on the body, since a person is only able to use two hands to hold the packs in place. Finally, because the hands of a person using this method will be occupied, the person will be unable to simultaneously engage in other activities that require use of the hands.

Another method for applying a thermal transfer element to a body part is to physically attach the pack to the body part. Straps, wraps, adhesives, and other means have all been used for that purpose, but all still have several disadvantages. First, the person's movement can be restricted by attachment of thermal transfer elements to certain commonly treated parts, such as the knee. Additionally, a user is likely to find it cumbersome to hold the pack in place with one hand while simultaneously trying to use a strap or other means to secure the pack in place. Furthermore, attaching a thermal transfer element too tightly can impede circulation and cause tissue damage by disrupting blood flow through the treated body part. Finally, it is difficult to physically attach a thermal transfer element to certain body parts, such as the back, without engaging the assistance of another.

Many devices and methods have been developed over the years to solve these problems. US 2006/0218692 to Lamarque (publ October 2006), for example, teaches positioning of thermal transfer elements, vibrators, magnets, and a host of other therapeutic components within the cavities of pockets located about a jacket or other garment. Others place thermal pads in pockets of scarves (see U.S. Pat. No. 5,086,629 to Dibrell, February 1992) and cuffs for various parts of the body (see U.S. Pat. No. 4,985,924 to Perry, January 1991, and U.S. Pat. No. 4,625,729 to Roney, December 1986). These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

It turns out that using pockets to position thermal pads, however, is not an especially good solution. Among other things, the location of the thermal transfer element is predetermined by the location of the pockets. U.S. Pat. No. 5,887,437 to Maxim, March 1999 tries to solve that problem by adhering a thermal transfer element directly to the skin. But of course devices using that concept can be extremely uncomfortable.

US 2006/0213156 to Nilfuroshan, (publ. September 2006) teaches a horse blanket, the underside of which has a hook-and-loop attachable material that releasably couples mating material on one or more pockets. The pockets (referred to as cavities) are sized and dimensioned to receive thermal transfer elements, and by moving around the pockets a user can position the thermal transfer elements substantially anywhere on the underside of the blanket. In that application, the concept was directed to non-human animals, which presumably would tolerate a blanket with a plurality of pockets facing the skin.

What is still needed is a method of expanding the horse blanket concept to human clothing, so that a user could position thermal transfer elements around the body, without having a plurality of pockets facing the bare skin of the wearer.

SUMMARY OF THE INVENTION

The present invention provides apparatus, systems and methods in which an item of human clothing has inner and outer flexible layers that define a space sufficiently large to position a thermal transfer element in any of multiple, non-overlapping positions.

In preferred embodiments the space and the thermal transfer element have cooperating sides of a hook-and-loop attachment. For example, the inner surface of the outer layer can include a knit or woven fabric, or a napped or looped material, and a facing side of the thermal transfer element (or its housing) can include a hooked material.

All suitable items of clothing are contemplated, but especially a shirt, jacket or pants that appear to others as a substantially normal garment. Athletic jackets, "sweats" and other sporting-related garments are especially contemplated, with the inner and outer layers comprising cotton, nylon, or other fabrics known to the industry, including performance fabrics.

Each space has one or more openings, in either the inner or outer layers, and preferably at the shoulders or sides of the torso, or at the pocket areas of pants. The openings can be merely slits, or can have a suitable closure, for example a flap or a zipper.

The spaces are preferably large, not only relative to the size of a corresponding thermal transfer element, but also to the size of the garment. For example, a shirt or jacket can have a space extending across the entire upper or lower back regions, or along the entire left and right front panels. Contemplated spaces can alternatively extend across the entire back or front (for pullovers) or even a single contiguous space across the entire back and front. From a numerical perspective, a wall of a space having a hook-and-loop attachment material can advantageously have an area of at least 200-1000 cm². Similarly, preferred clothing can be adjusted so that a space has a volume of at least 1000-8000 cm³. These and all other ranges specified herein should be construed as inclusive of their endpoints.

Thermal transfer elements can have any suitable configuration, and can be enclosed or otherwise coupled to any sort of holder. For example, a thermal transfer element can consist of a single gel pack, or multiple gel packs coupled at flex points. Alternatively, a thermal transfer element can include one or more plastic gel packs housed within a fabric covering. Most preferably, thermal transfer elements are replaceably disposed in a pouch with a zipper, flap, or other closure, and have a hook or loop material disposed on one of its outer sides. Such pouches preferably have a thermal insulation on that side, and have only a very thin, thermally transmissive, fabric on the other side.

There are many advantages to the various embodiments of the present invention. An advantage of one embodiment is the ability to adjustably secure a thermal transfer element to any body part covered by the garment. In this embodiment, the location of the thermal transfer element is adjustable over substantially an entire surface of an article of clothing because the fastener on the article of clothing is not fixed in a single location. Instead, in this embodiment, the fastener substantially covers an entire surface of the article of clothing. Thus a user of this embodiment of the present invention can precisely and adjustably target any body part covered by the article of clothing, instead of only specific, unchangeable locations.

Another advantage of an embodiment of the present invention is the ability to adjustably secure a thermal transfer element to an article of clothing multiple times without weakening the strength of the engagement between the fasteners. Other systems, which use adhesives to secure thermal transfer elements to an article of clothing, do not have this advantage because the adhesive weakens after every adhesion. Eventually, after multiple adhesions, the adhesive will no longer hold the thermal transfer element to the article of clothing. The engagement between fasteners of an embodiment of the present invention, however, does not so weaken due to repeated use.

Another advantage of an embodiment of the present invention is that it allows a person to apply a thermal transfer element to a hard to reach area, such as the back, without requiring the assistance of another. The person can simply secure the thermal transfer element to the back of the article of clothing before putting on the article of clothing. In other systems, it is very awkward or cumbersome to apply a thermal transfer element to the back without the assistance of another.

Another advantage of an embodiment of the present invention is that it allows a user to apply a thermal transfer element to a body part without occupying the hands. Thus, the user can engage in activities that require the use of one or both hands while a thermal transfer element is held against a body part. A further, related advantage is the ability to hold multiple thermal transfer elements, including both hot and cold thermal transfer elements simultaneously, to multiple body parts. Manual systems are limited by the number of thermal transfer elements the person can hold in the hands. The present invention, however, is not so limited.

A further related advantage of an embodiment of the present invention is the ability to engage in an athletic activity while a thermal transfer element is held against a body part. An athlete wearing a garment of the present invention is able to keep body parts warm during periods of inactivity, and need not remove the garment prior to resuming the athletic activity. Wearing the garment during the athletic activity can also prevent injury to muscles by keeping them warm. Alternatively, an athlete can cool parts of the body during strenuous activity to prevent overheating. Furthermore, a thermal transfer element secured to a body part can act as padding for that body part. Finally, after the athletic activity, the garment can be used for treatment of sore muscles.

Yet another advantage of an embodiment of the present invention is the ability to press a thermal transfer element against a body part. When the article of clothing snugly fits the body of the wearer, and when the thermal transfer element is secured inside the article of clothing, the snug fit presses the thermal transfer element against the body part. The term "snug fit" means that the article of clothing is tight on the wearer's body, having little or no slack in the material. The term "press," as used in this context, means a force exerted on the thermal transfer element and toward the body of the wearer. This pressure increases the efficiency of heat transfer by increasing the surface area of the thermal transfer element in contact with the body part, because any gaps between the surface of the thermal transfer and the body part will be flattened out. Furthermore, pressure is also helpful for preventing swelling of an injured body part when a cold pack is applied.

These and other objects, features, aspects and advantages of the inventive subject matter will become more apparent from the following detailed description of preferred embodiments, along with the accompanying drawings in which like numerals represent like components.

BRIEF DESCRIPTION OF THE DRAWINGS

FIG. 5 is a front elevation view of a pouch for enclosing a thermal transfer element.

FIG. 6 is a back elevation view of the pouch of FIG. 5.

FIG. 7 is a front elevation view of a thermal transfer element.

FIG. 8 is a side perspective view of the pouch of a thermal transfer element according to one embodiment of the invention, before and after a thermal transfer element is inserted into a pouch.

FIG. 15 is a front perspective view of the inside of an article of clothing comprising an inflatable air bladder, according to another embodiment of the invention.

FIG. 16 is a front perspective view of the outside of a garment comprising the article of clothing of FIG. 15, shown with the air bladder inflated and thermal transfer elements in place, according to one embodiment of the invention.

FIG. 17 is a back perspective view of the garment of FIG. 16.

FIG. 21 is a side perspective view of a thermal transfer element secured in place inside an article of clothing by a cinch cord, according to one embodiment of the invention.

FIG. 22 is a front perspective view of a garment with the thermal transfer element of FIG. 21 secured inside the article of clothing.

FIG. 23 is a back perspective view of the garment of FIG. 22.

DETAILED DESCRIPTION

Figure 1:
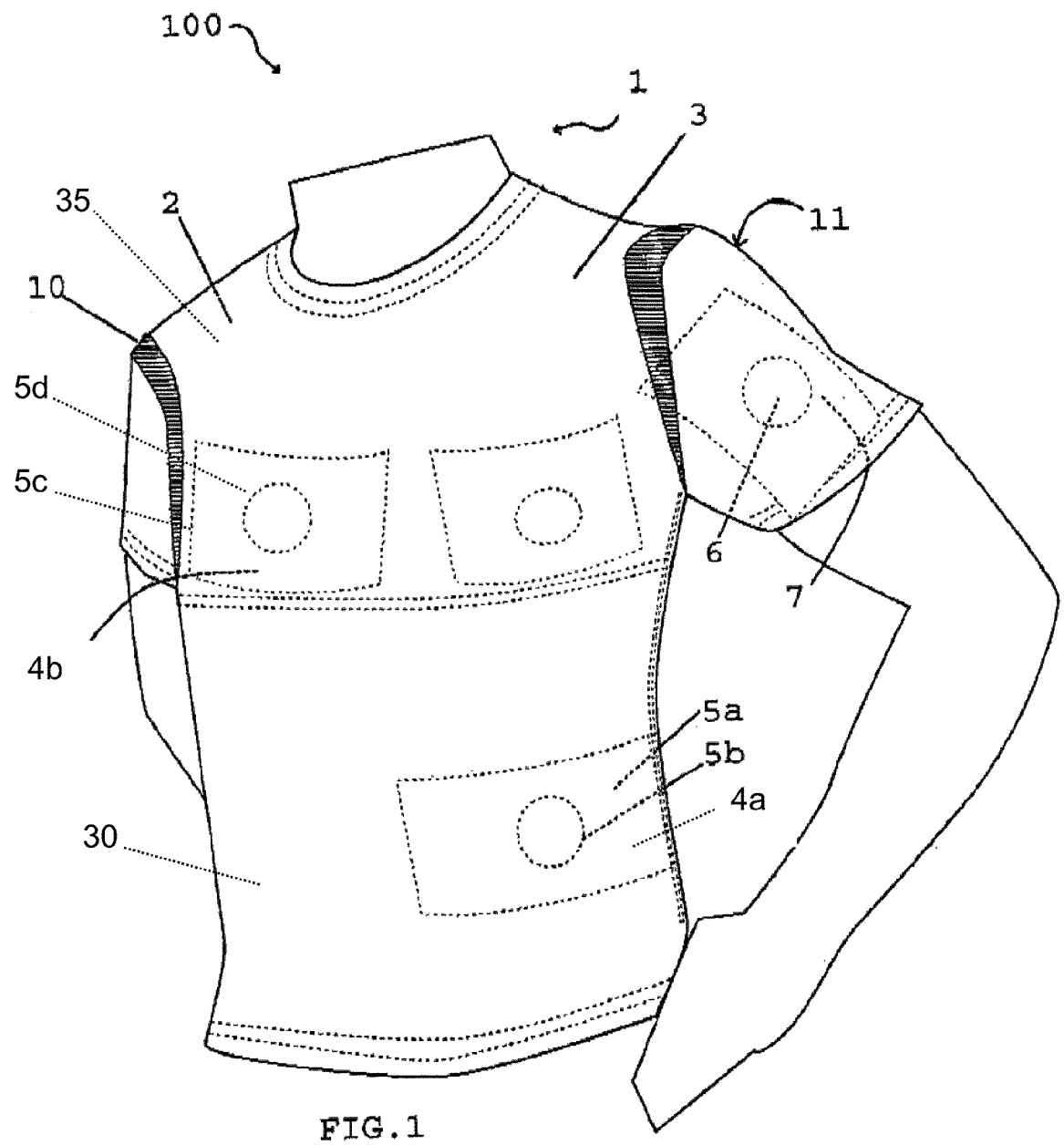
FIG. 1 is a front perspective view of a sports shirt or jacket having inner and outer layers that define several spaces for receiving thermal transfer elements.
Figure 2:
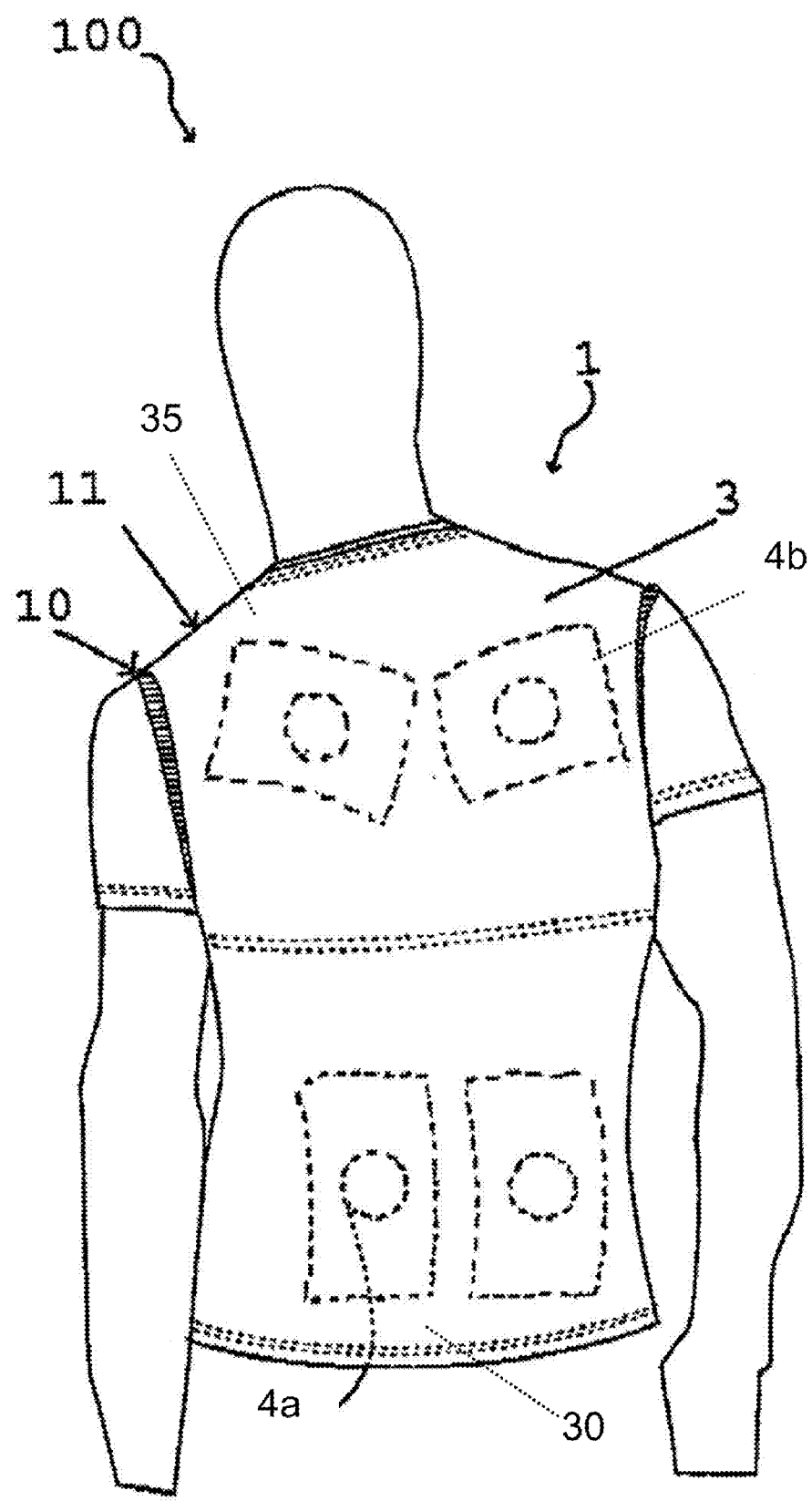
FIG. 2 is a back perspective view of the garment of FIG. 1.
Figure 3:
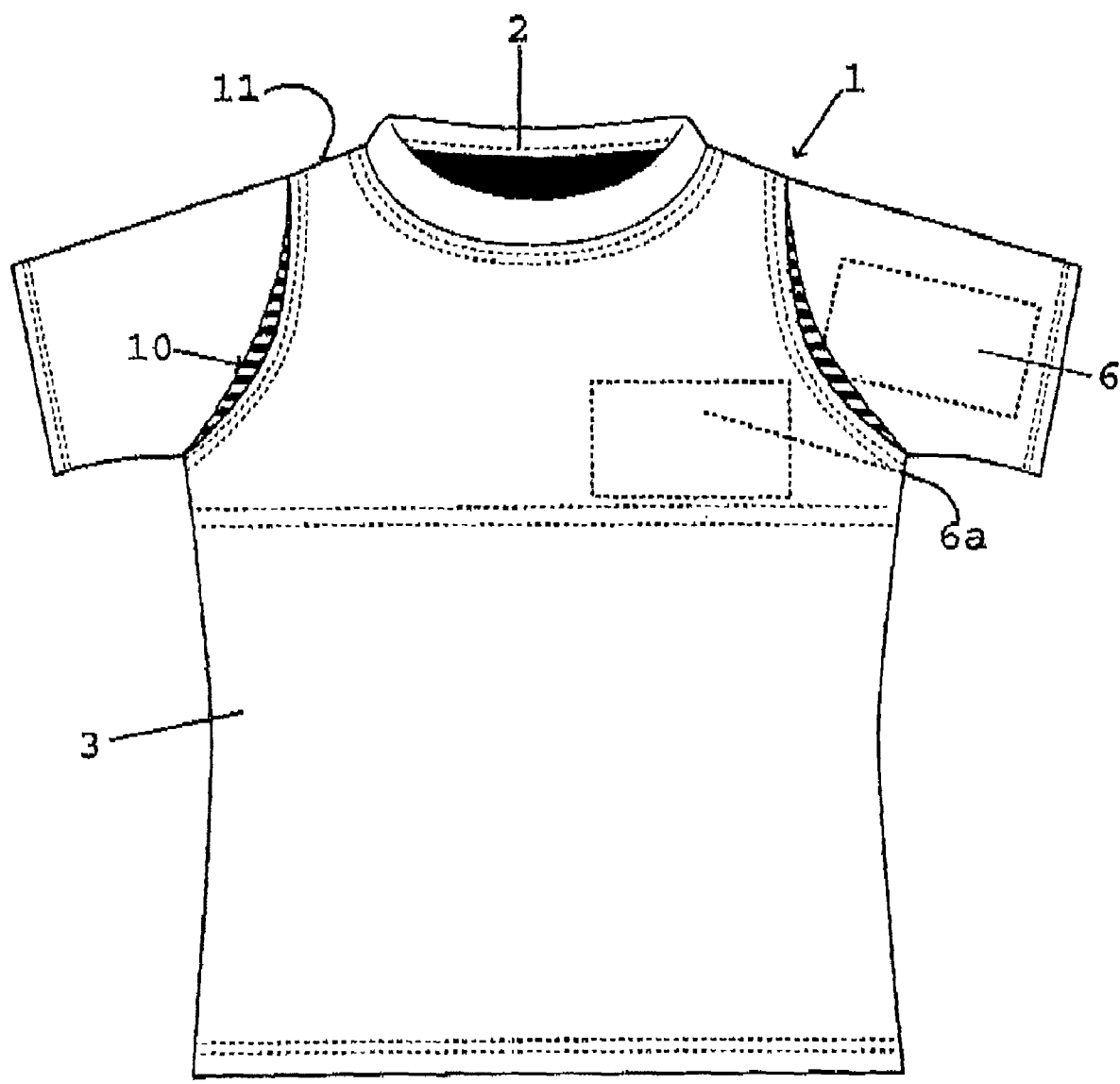
FIG. 3 is a front elevation view of the garment of FIG. 1.

FIGS. 1 to 3 generally depict a garment 100 having a first layer 10, an outer layer 11, a thermal transfer element 4, a first fastener 5A, and a second fastener 5B. The garment 100 is the entire combination; the article of clothing 1 is the piece of apparel to which thermal transfer elements are secured. Article of clothing 1 has first 30 and second spaces 35, each of which can be defined by the first layer 10 and outer layer 11. As shown in FIGS. 1-2, the first space 30 extends around the front, sides, and lower back region of the article of clothing 1.

An engagement between the first fastener 5A and the second fastener 5B removably and adjustably secures the thermal transfer element 4A to any location 6 on the interior surface 2 of the outer layer 11 of the article of clothing 1. Likewise, an engagement between a third fastener 5C of the second space 35 and a fourth fastener 5D removably and adjustably secures the thermal transfer element 4B to any location 6 on the interior surface 2 of the outer layer 11 of the article of clothing 1. "Removably and adjustably" secured means that the thermal transfer element can be removed without damaging the fasteners or otherwise dismantling the garment, and can be reattached in a different location. After attachment, heat transfer takes place between the thermal transfer element 4 and a body part 7 in contact with the location 6 on the article of clothing 1 where the thermal transfer element 4 is secured. The location 6 is "in contact" with the body part 7 even if there are one or more layers of material between the location 6 and the body part 7. In other words, it is not necessary for the location 6 to touch the skin of the body part 7 for the location 6 to "contact" the body part 7, so long as they immediately adjoin each other.

Figure 4:
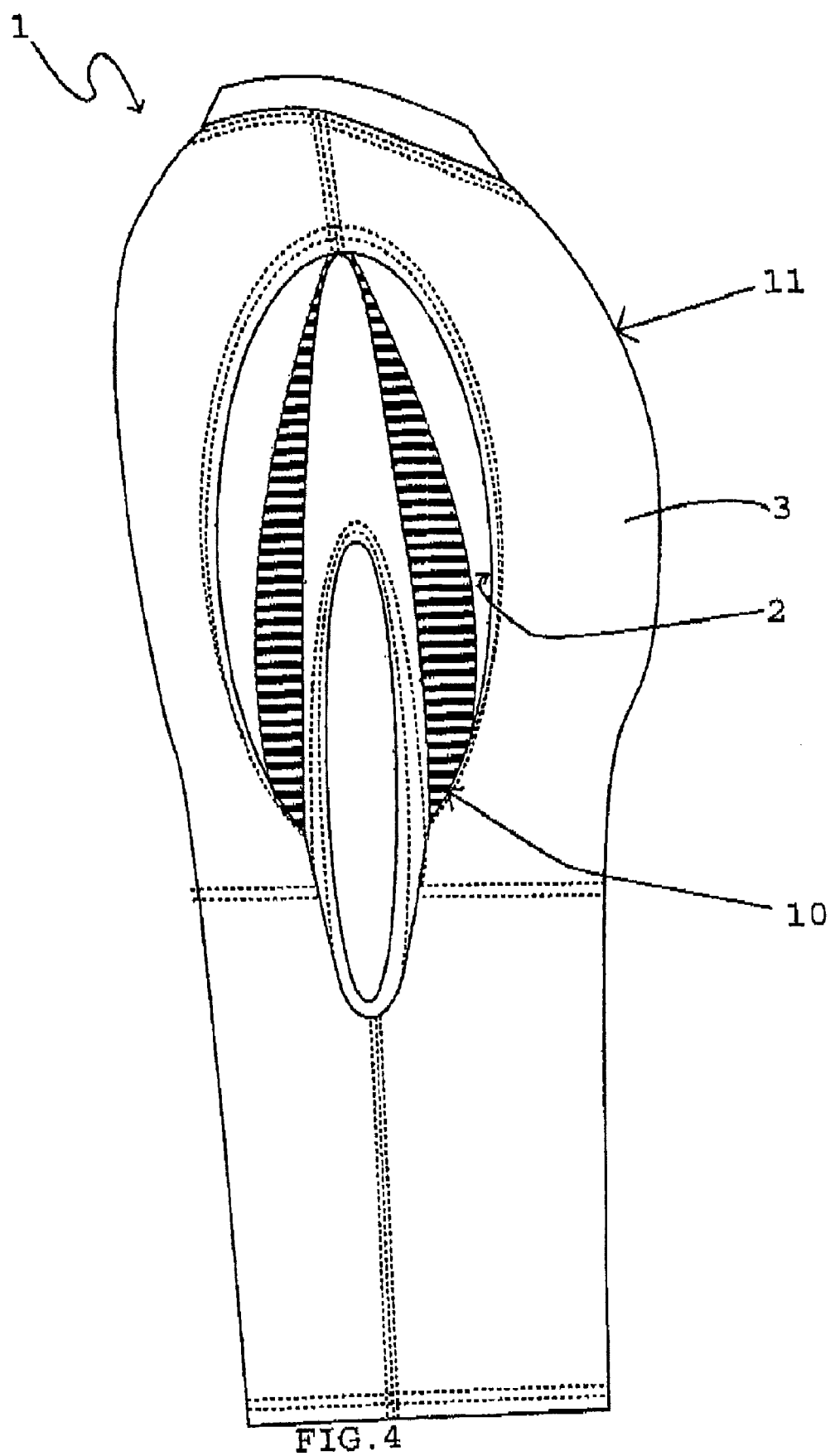
FIG. 4 is a side elevation view of the garment of FIG. 1, showing a shoulder opening into front and rear spaces.
Figure 10:
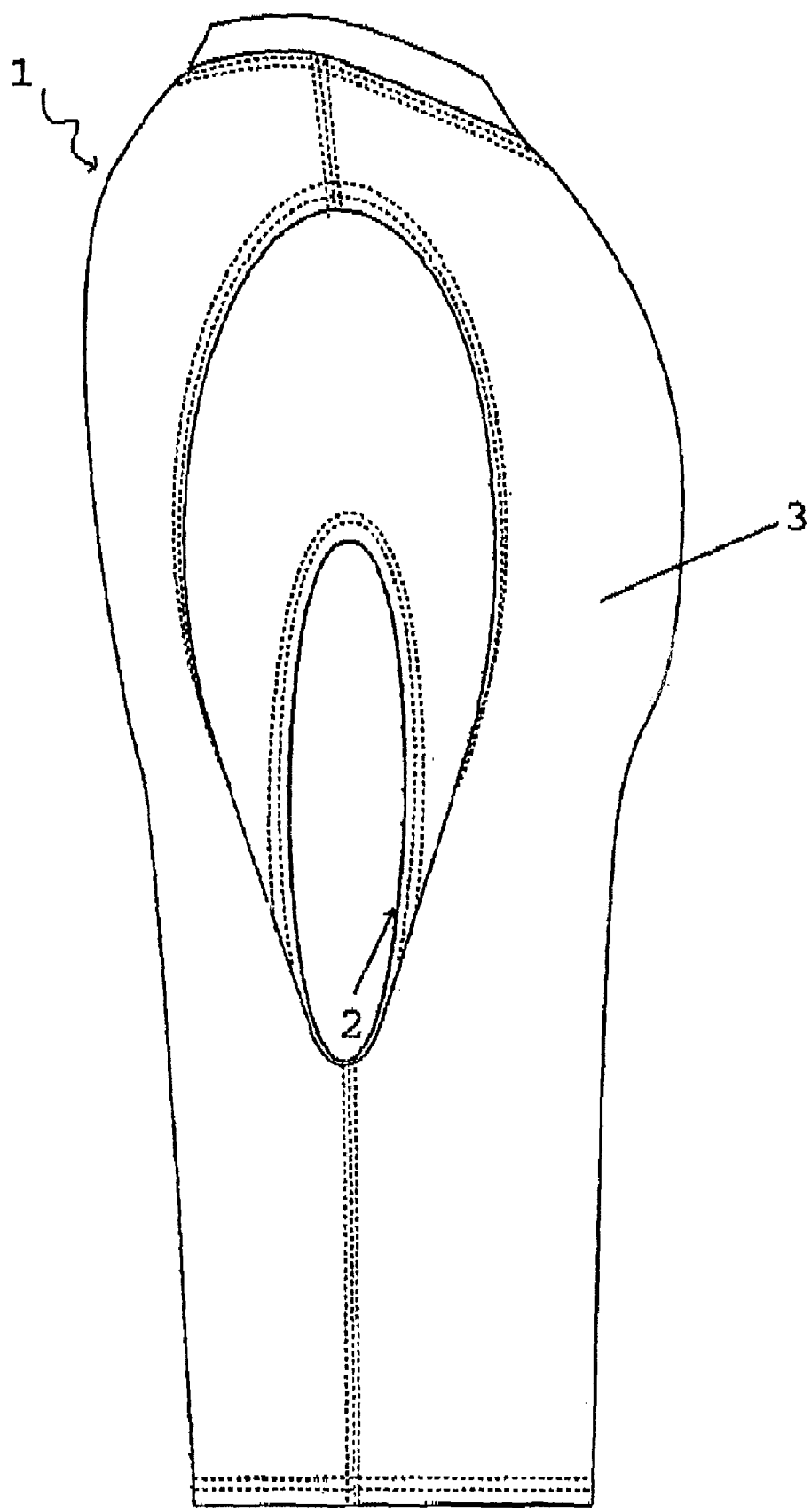
FIG. 10 is a side elevation view of the article of clothing of the garment of FIG. 9.
Figure 11:
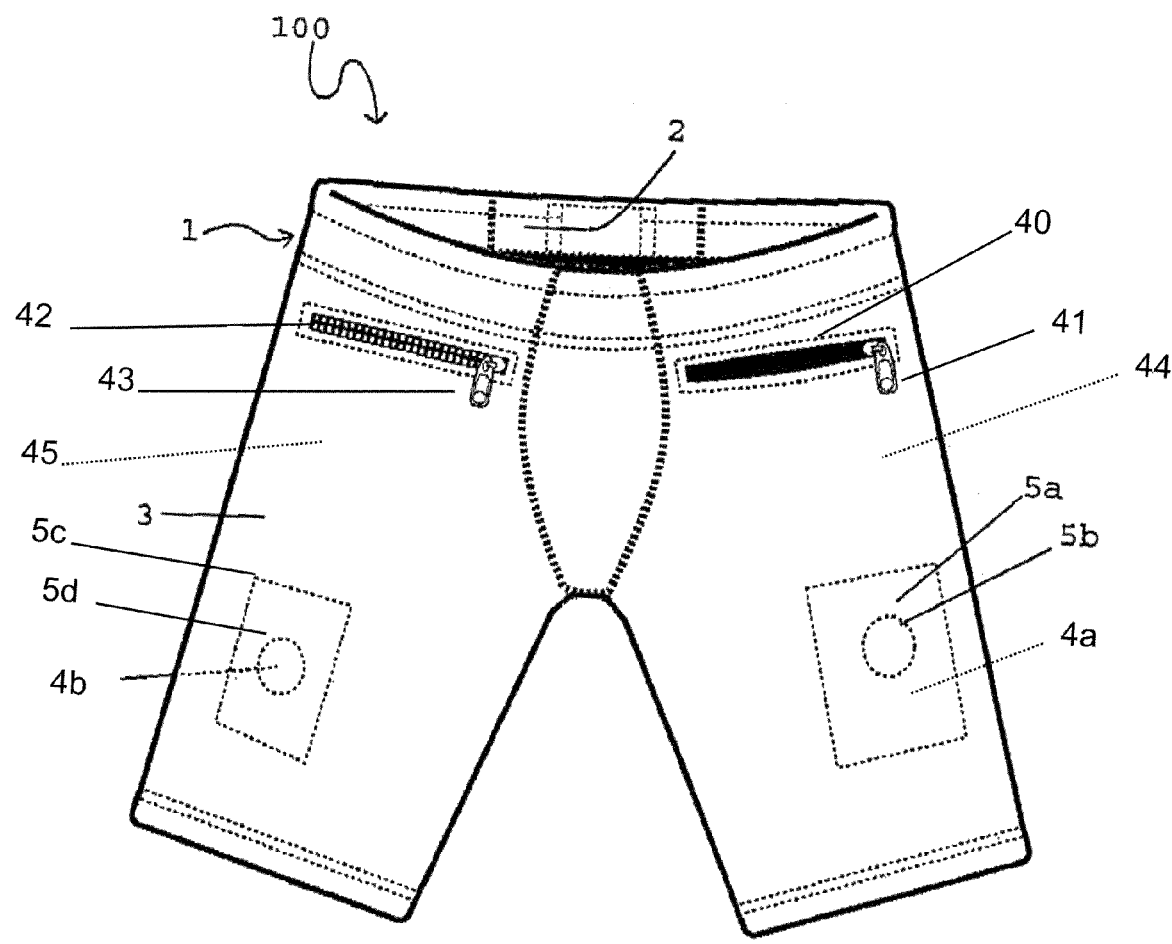
FIG. 11 is a front perspective view of a garment comprising a different article of clothing (namely shorts), according to another embodiment of the invention.

As best illustrated in FIGS. 4, 10 and 11, an interior surface 2 of the article of clothing 1 is any surface of any layer of the article of clothing that faces inwardly toward the wearer. An exterior surface 3 of the article of clothing 1 is any surface of any layer of the article of clothing 1 that faces outwardly away from the wearer.

In an exemplary embodiment, as best illustrated in FIG. 4, the article of clothing has a first layer 10 and an outer layer 11 such that there is a space for thermal transfer elements 4 between the layers. In an exemplary embodiment, the outer layer 11 is made from a nylon, polyester, and spandex blend, and the interior surface 2 of the outer layer 11 is brushed to create loop material suitable for a hook and loop fastener. The process of brushing is well known in the art, and is essentially a finishing process for materials, particularly knit or woven fabrics, in which brushes or other devices abrade the material to create a looped or napped surface that is suitable for use in a hook and loop fastener. The first layer 10 can be any flexible material but in an exemplary embodiment is a fine mesh material.

The article of clothing 1 can be made from any flexible material. More specifically, and without limitation, the material can be moisture absorbent, breathable, stretchable, meshed, or any blend or combination thereof. Even more particularly, the material can be a blend of nylon, polyester, and spandex. The material can also be thermoconductive in order to better conduct heat between the thermal transfer element 4 and the body part 7, or thermoreflective to help keep heat inside the article of clothing 1. The material can further comprise either the first fastener 5A or the second fastener 5B, meaning that these fasteners can be either an integral part of the material or affixed thereto. For example, one or more surfaces of the article of clothing 1 can be brushed such that it comprises loop material suitable for a hook and loop fastener.

The article of clothing 1 can be of any type including, without limitation, shirts, vests, shorts, pants, bodysuits, skirts, dresses, robes, and so forth, provided they can be configured to include a sufficiently large space for receiving the thermal transfer elements. From a numerical perspective, a wall of a space having a hook-and-loop attachment material can advantageously have an area of at least 200 cm$^2$, 400 cm$^2$, 600 cm$^2$, 800 cm$^2$ or even 1000 cm$^2$. Similarly, preferred clothing can be adjusted so that a space has a volume of at least 1000 cm$^3$, 2000 cm$^3$, 4000 cm$^3$, 6000 cm$^3$, or even 8000 cm$^3$. The jacket of FIGS. 1-4, should be interpreted as having a space with a wall having an area at least 1000 cm$^2$, and a volume of at least 8000 cm$^3$.

Figure 12:
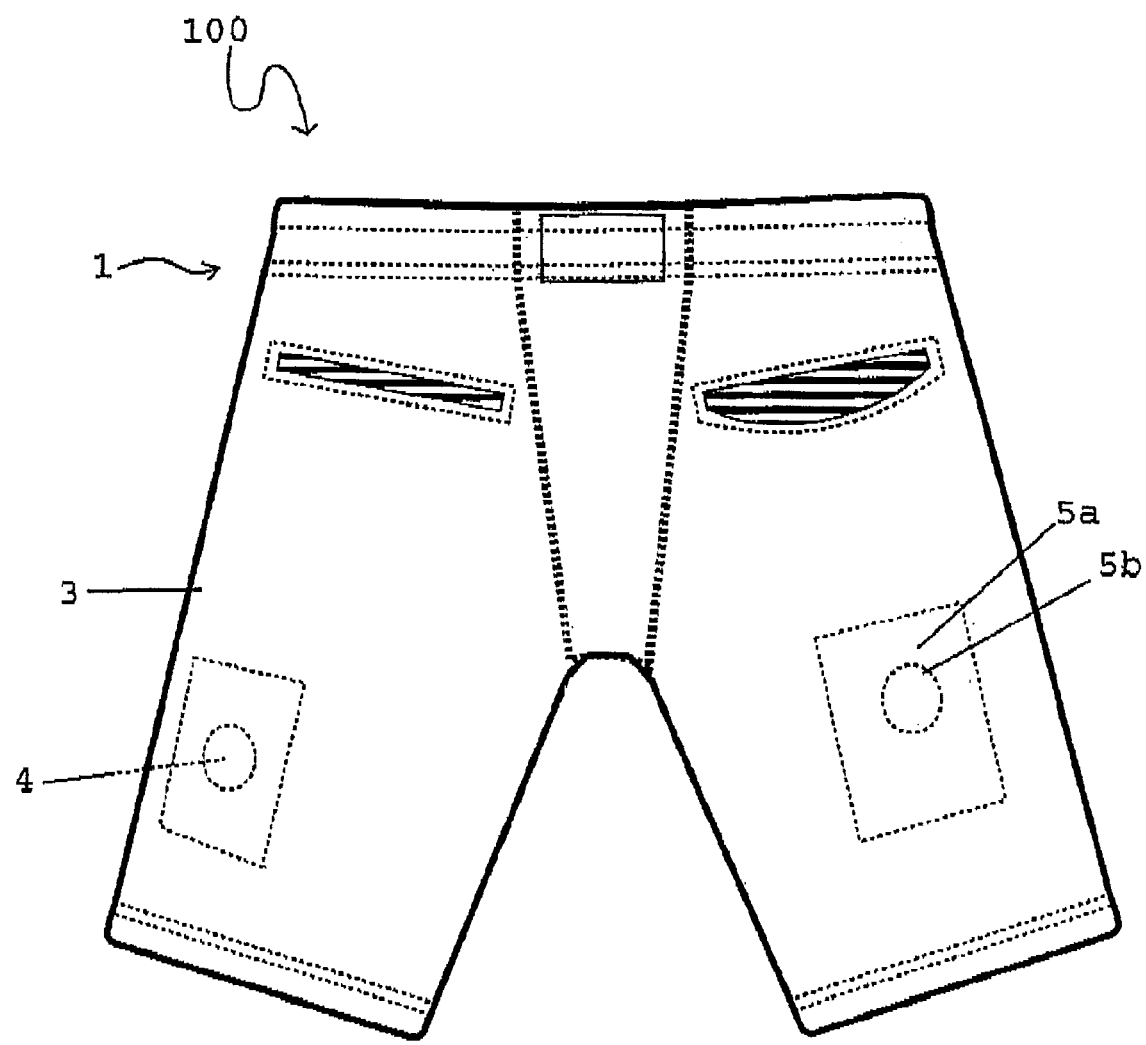
FIG. 12 is a back elevation view of the garment of FIG. 11.

For example, as shown in FIGS. 11 and 12, the article of clothing 1 can be a pair of shorts. It can come in a variety of shapes and sizes to accommodate the body shapes of men, women, and children of all sizes. The article of clothing 1 is worn on the body of a person, and can be worn as any layer of clothing, including as an undergarment or as an over-garment. In an exemplary embodiment of the invention, the article of clothing 1 snugly fits the body of the wearer such that any thermal transfer element 4 inside the article of clothing 1 is pressed against the body part 7 due to the snug fit of the article of clothing 1. Article of clothing 1 includes first 40 and second openings 42 that have respective first 41 and second closure mechanisms 43. The first 40 and second openings 42 provide access to respective first 44 and second spaces 45 that each extends downwardly into a lower region of the article of clothing 1.

In FIGS. 5 to 8, a pouch 8 has a cavity sized and dimensioned to receive a thermal transfer element 9, and further has a hook or loop region 5b for attachment to a wall of a space in the article of clothing 1. The pouch 8 can be made of any suitable material including natural and synthetic textiles, plastics, and rubbers, and it can be made of the same materials that the article of clothing 1 comprises. In an exemplary embodiment, the pouch 8 is approximately six inches by ten inches (about 15×25 cm) and has two sides that are sewn together to form a pouch. One side of the pouch 8 can be made of Thinsulate® laminated with variations of tricot, the other side of a mesh material which can be a blend of polyester and spandex. Thinsulate® is the registered trademark name of a material made by 3M Company (St. Paul, Minn.) that comprises thin and relatively dense polyolefin microfibers and polyester fibers. The two sides of the pouch 8 can be sewn together along three edges, leaving an opening on the fourth edge. Optionally the pouch 8 is closable on the fourth edge so that the thermal transfer element 9 can be completely enclosed in the pouch 8, as shown in FIG. 8. The closure can be zipper, snap, button, or the like, but in an exemplary embodiment is a hook and loop fastener. The pouch 8 also comprises the second fastener 5B, meaning that this fastener can be either an integral part of the pouch 8 or attached thereto. In an exemplary embodiment, the second fastener 5B is hook material and is sewn to the Thinsulate-tricot side of the pouch 8.

The thermal transfer element 9 is any object suitable for transferring heat including, without limitation, heat packs and cold packs of the type commonly used as hot or cold compresses on injured or sore body parts, whether single-use or reusable. The thermal transfer element 9 can contain water, ice, metal, gel, or any other material, whether solid, liquid, or gas. Examples of some types of thermal transfer elements include, without limitation, the Hot & Cold Flexible Gel Pack (3M, St. Paul, Minn.), Thermo-Pad Heat Packs (Hood Thermo-Pad, Summerlend, BC Canada), and the Hot/Cold Reusable Gel Pack (Accu-Therm, Taipei, Taiwan). The thermal transfer element 9 is brought to a desired temperature prior to attachment of the thermal transfer element 4 to the article of clothing 1 or, if possible, while the thermal transfer element 4 is attached. The thermal transfer element 9 can be heated or cooled in any suitable manner, including without limitation, convection, conduction, radiation, electrical resistance, and chemical reaction. For example, the thermal transfer element 9 can be cooled in a refrigerator, freezer, ice water bath, or endothermic chemical reaction. The thermal transfer element 9 can be heated, for example, in an oven, microwave, hot water bath, or exothermic chemical reaction.

In an exemplary embodiment of the present invention, as best illustrated in FIGS. 1 and 2, the thermal transfer elements 4A and 4B are adjustably secured to the interior surface 2 of the outer layer 11 of the article of clothing 1 by the engagement of first fastener 5A and second fastener 5B, and third fastener 5C and fourth fastener 5D, respectively. As seen in FIG. 3, the thermal transfer element 4 can be removed from an initial location 6 by disengagement of the fasteners, and re-secured in a different location 6A by reengagement of the fasteners. The ability to disengage and reengage the fasteners in a new location 6A makes the location 6 of the thermal transfer element 4 adjustable.

The first fastener 5A can be found anywhere on the article of clothing 1, including anywhere on any interior surface 2 or exterior surface 3. In one embodiment, the first fastener 5A covers substantially an entire surface of the article of clothing 1. In an exemplary embodiment, the first fastener 5A is loop material that covers substantially the entire interior surface 2 of the outer layer 11 of the article of clothing 1.

The second fastener 5B can be found anywhere on the thermal transfer element, including on a thermal transfer element 9. In an exemplary embodiment, as seen in FIGS. 6 and 8, the second fastener 5B is found on the thermal transfer element 4, specifically on the back of the pouch 8. The first fastener 5A and the second fastener 5B are any type of complementary fasteners capable of repeatedly engaging and disengaging with each other, without significantly damaging either fastener or their ability to engage. It is not material which of the pair of complementary fasteners is the first fastener 5A or the second fastener 5B. For example, the first fastener 5A can be loop material and the second fastener 5B can be hook material. Likewise, the first fastener 5A can be hook material and the second fastener 5B can be loop material. In an exemplary embodiment of the present invention, however, the first fastener 5A is loop material that covers substantially the entire interior surface 2 of the outer layer 11 of the article of clothing 1, and the second faster 5B is hook material that is sewn to the back of the pouch 8 of the thermal transfer element 4. Because in this embodiment the first fastener 5A is loop material covering substantially the entire interior surface 2 of the outer layer 11, the thermal transfer element 4 is adjustable over any location on the interior surface 2 by disengagement and reengagement of the fasteners 5.

Figure 9:
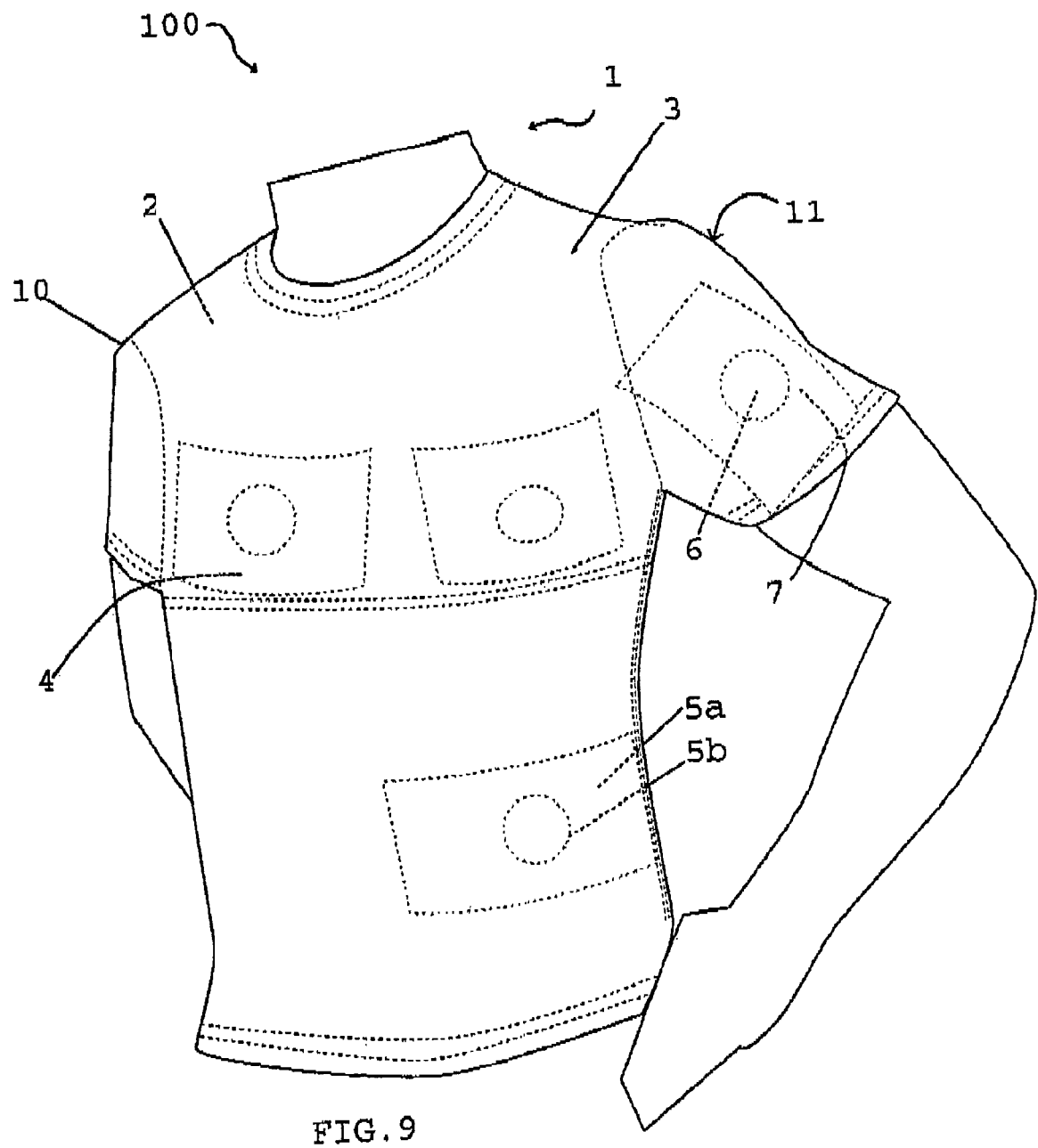
FIG. 9 is a front perspective view of a garment comprising an article of clothing having only a first layer, with hidden secured thermal transfer elements indicated with dashed lines, according to another embodiment of the invention.

In another embodiment of the present invention, best illustrated in FIG. 9, a garment 100 comprises an article of clothing 1 having an interior surface 2 and an exterior surface 3, a thermal transfer element 4, a first fastener 5A and a second fastener 5B. Unlike the previous embodiment, the article of clothing 1, as shown in FIG. 10, does not comprise a first layer plus an outer layer, but instead comprises only a first layer 10. In this embodiment, the thermal transfer element 4 is secured to the interior surface 2 of the first layer 10 of the article of clothing 1. As seen in FIG. 9, the thermal transfer element 4 is drawn with dashed lines to indicate that the thermal transfer element 4 is attached inside the article of clothing 1. The article of clothing 1 can be made from a blend of nylon, polyester, and spandex, and the interior surface 2 of the first layer 10 can be brushed to create loop material suitable for a hook and loop fastener. In another embodiment, the thermal transfer element 4 can be adjustably secured to the exterior surface 3 of the first layer 10 of the article of clothing 1. In this embodiment, the exterior surface 3 of the first layer 10 can be brushed to create loop material suitable for a hook and loop fastener.

Figure 13:
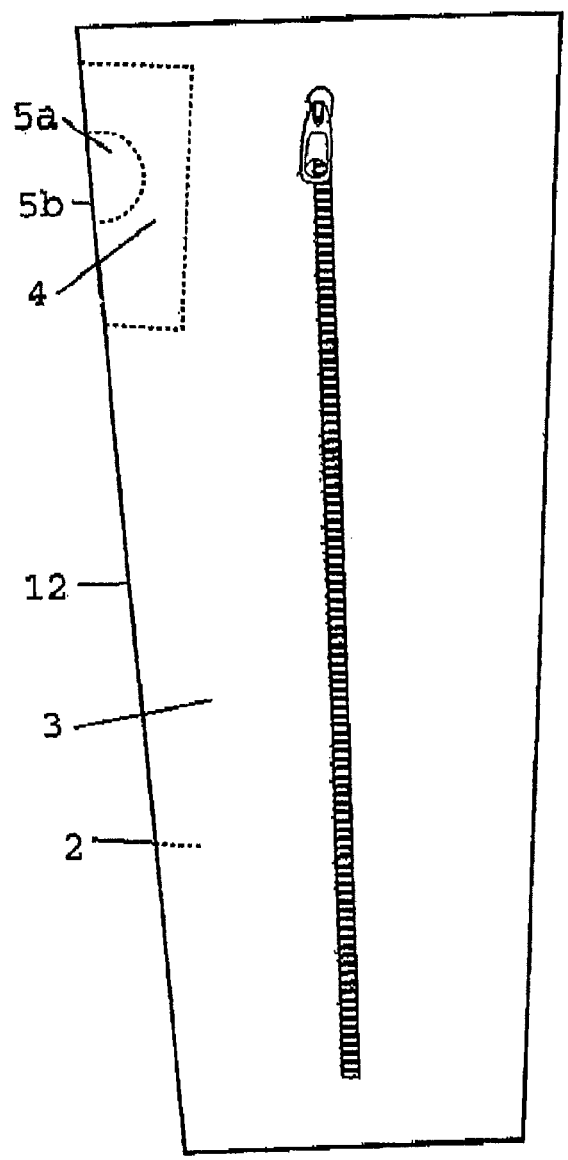
FIG. 13 is a front elevation view of a detachable segment of an article of clothing of a garment according to another embodiment of the invention.
Figure 14:
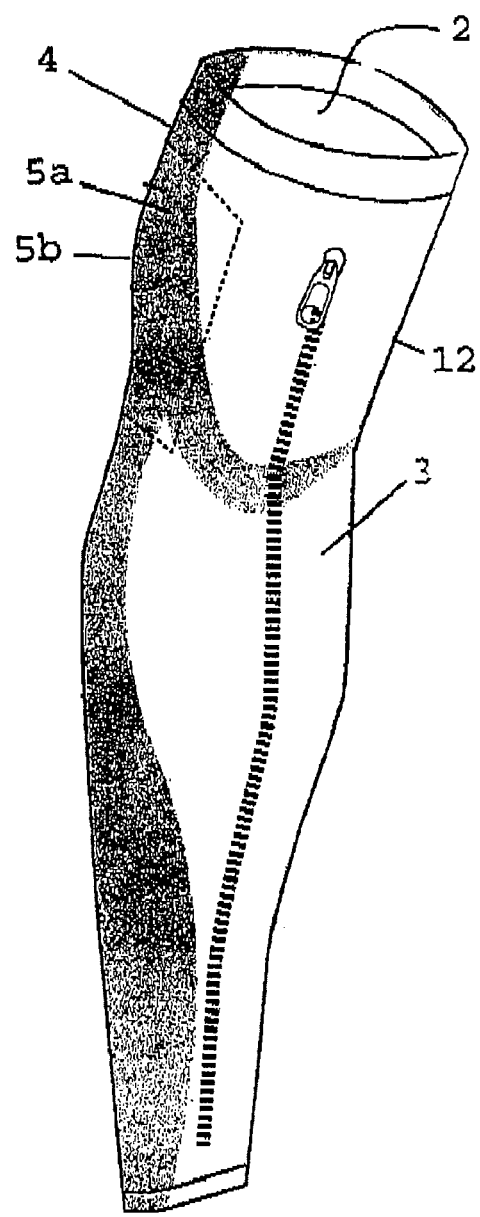
FIG. 14 is front perspective view of the garment of FIG. 13.

In another embodiment of the invention, the article of clothing 1 can comprise a detachable segment 12, such as a detachable sleeve for a shirt as illustrated in FIGS. 13 and 14. An article of clothing 1 can be worn with or without the detachable segment 12. Likewise, the detachable segment 12 can be worn without the rest of an article of clothing 1. The detachable segment 12 comprises the first fastener 5A, meaning that this fastener can be either an integral part of the detachable segment 12 or attached thereto.

In other embodiments of the present invention, best illustrated in FIGS. 15 to 21, a thermal transfer element 4 is pressed against the body of the wearer by the article of clothing 1. In one embodiment, this pressure results from the snug fit of the article of clothing 1 against the body of the wearer. In one embodiment, shown in FIGS. 15 to 17, the pressure provided by the article of clothing 1 is augmented by inflation of an air bladder 15 contained inside the article of clothing 1. The air bladder 15 can be inflated by a one-way valve for receiving pressurized air, such as by a person blowing into the valve. The air bladder 15 can also be inflated by a small pump built into the air bladder 15. After placing the thermal transfer element 4 in a desired location inside the article of clothing 1, the user inflates the bladder 15, thus providing increased pressure on the thermal transfer element 4 as the interior surface of the air bladder 15 expands toward the wearer.

Figures 19, 20:
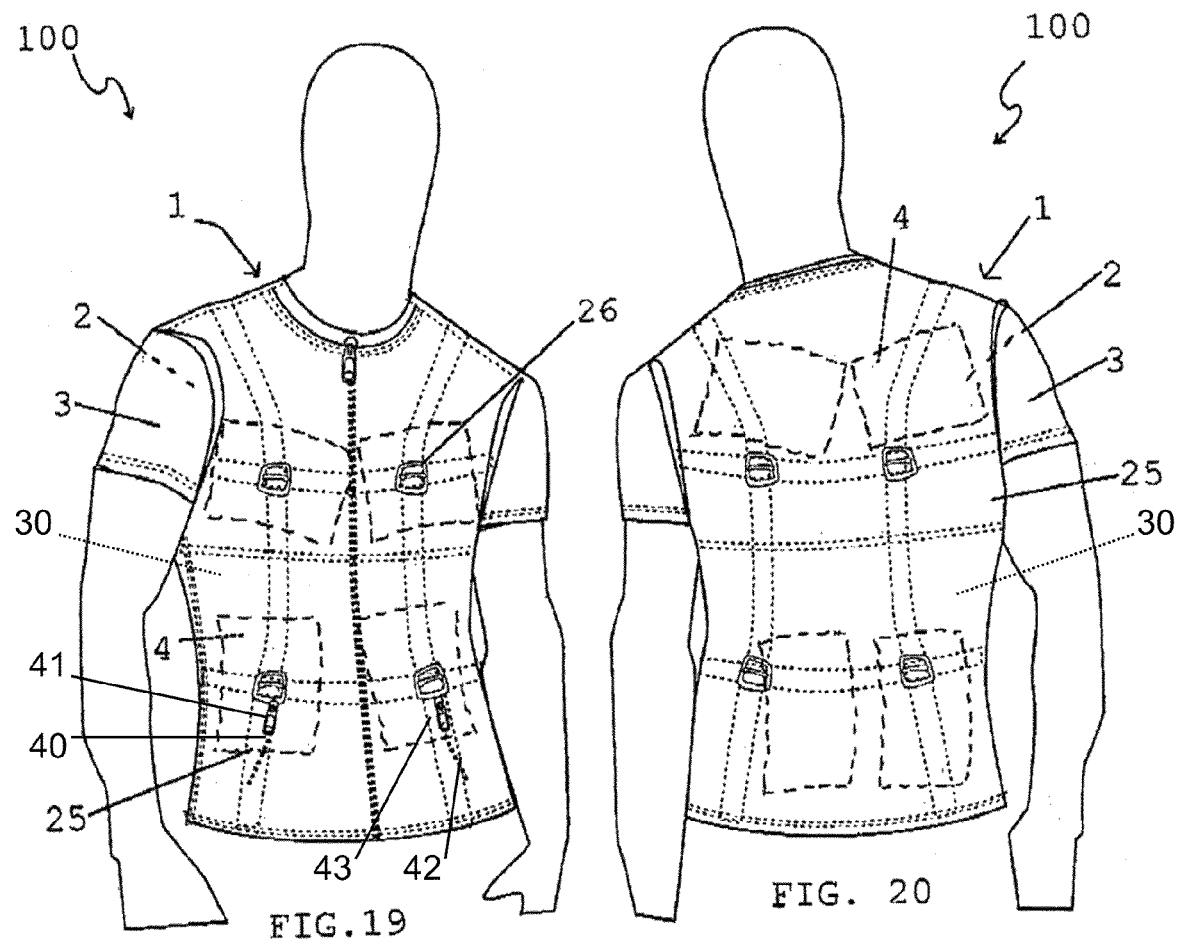
FIG. 19 is a front perspective view of a garment with the thermal transfer element of FIG. 18 secured inside the article of clothing.
FIG. 20 is a back perspective view of the garment of FIG. 19.
Figure 18:
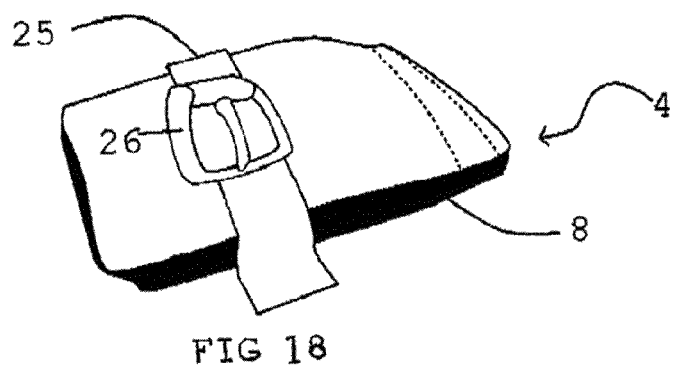
FIG. 18 is a side perspective view of a thermal transfer element held in place inside an article of clothing by a strap and buckle, according to another embodiment of the invention.

In another embodiment, as seen in FIGS. 18 to 20, the pressure against the thermal transfer element 4 is augmented by tightening straps 25 connected to buckles 26. After the user places the thermal transfer element 4 in a desired location, the user tightens the straps 25 using the buckles 26, thus providing increased pressure on the thermal transfer element 4.

In another embodiment, shown in FIGS. 21 to 23, the pressure is augmented by tightening cinch cords 35 that run throughout the article of clothing 1. After the user places the thermal transfer element 4 in a desired location, the user pulls on the cinch cord 35, thus providing increased pressure on the thermal transfer element 4.

A method of use according to an exemplary embodiment of the present invention is best understood with reference to FIGS. 1 to 8 and comprises the following steps: selecting a body part 7 to have a thermal transfer element 9 applied to it, putting on an article of clothing 1, selecting a location 6 on the article of clothing 1 that contacts the selected body part 7 and has a first fastener 5A, bringing a thermal transfer element 9 to a desired temperature, engaging the first fastener 5A with the second fastener 5B to removably and adjustably secure the thermal transfer element 9 to the article of clothing 1, and transferring heat between the thermal transfer element 9 and the body part 7. The thermal transfer element 9 can be secured to the article of clothing 1 while the article of clothing 1 is being worn, while it is not being worn, or while it is partially being worn. Heat transfer continues until the thermal transfer element 9 reaches approximately the same temperature as the body part 7, at which point heat transfer begins to cease. In one embodiment, the second fastener 5B is affixed to the thermal transfer element 9. In an exemplary embodiment, the thermal transfer element 9 is enclosed in a pouch 8 with the second fastener 5B, preferably hook material, affixed to one side of the pouch 8. Furthermore, the above steps can be repeated in any order to attach a plurality of thermal transfer elements 9 to a plurality of locations 6 contacting a plurality of body parts 7. These plurality of thermal transfer elements 9 can be any combination of hot packs and cold packs.

Another method of use of the present invention, best understood with reference to FIGS. 1 to 8, is a method of heating or cooling the body of an athlete while the athlete is engaged in an athletic activity, comprising the steps of selecting a body part 7 of an athlete to be heated or cooled, selecting a location 6 on the article of clothing 1 that contacts the selected body part 7 when the article of clothing 1 is worn and having a first fastener 5A, bringing a thermal transfer element 9 to a desired temperature, removably and adjustably securing the thermal transfer element 9 to the article of clothing 1 so that the thermal transfer element 9 is contacting the body part 7, and transferring heat between the body part 7 and the thermal transfer element 9 while the athlete is engaged in an athletic activity. Because the garment 100 holds the thermal transfer element 9 in place, the athlete's hands are free to participate in the athletic activity. In one embodiment, the second fastener 5B is affixed to the thermal transfer element 9. In an exemplary embodiment, the thermal transfer element 9 is enclosed in a pouch 8 with the second fastener 5B, preferably hook material, affixed to one side of the pouch 8. Furthermore, the above steps can be repeated in any order to attach a plurality of thermal transfer elements 9 to a plurality of locations 6 contacting a plurality of body parts 7, so that more heat can be transferred to or from the athlete's body.

Another method of use of the present invention, best understood with reference to FIGS. 1 to 8, is a method of performing physical therapy on a patient, comprising the steps of selecting a body part 7 that will receive physical therapy, putting the article of clothing 1 on the body of the patient, selecting a location 6 on the article of clothing 1 that contacts the selected body part 7 and has a first fastener 5A, bringing a thermal transfer element 9 to a desired temperature, removably and adjustably securing the thermal transfer element 9 to the article of clothing 1 by engaging a first fastener 5A and a second fastener 5B, and transferring heat between the thermal transfer element 9 and the selected body part 7 while the patient simultaneously receives physical therapy on the selected body part 7. In one embodiment, the second fastener 5B is affixed to the thermal transfer element 9. In an exemplary embodiment, the thermal transfer element 9 is enclosed in a pouch 8 with the second fastener 5B, preferably hook material, affixed to one side of the pouch 8. Furthermore, the above steps can be repeated in any order to attach a plurality of thermal transfer elements 9 to a plurality of locations 6 contacting a plurality of body parts 7. A further method of use of the present invention, also best understood by reference to FIGS. 1 to 8, is a method of warming the body of a person in a cold environment, comprising the steps of selecting a body part 7 to be warmed, putting an article of clothing 1 on the body of the person, selecting a location 6 on the article of clothing 1 that contacts the selected body part 7 when the garment is worn and having a first fastener 5A, heating a thermal transfer element 9 to a desired temperature, removably and adjustably securing the thermal transfer element 9 to the selected location 6 by engaging first fastener 5A and second fastener 5B, and transferring heat from the thermal transfer element 9 to the body part 7 in order to stay warm longer in a cold environment. In one embodiment, the second fastener 5B is affixed to the thermal transfer element 9. In an exemplary embodiment, the thermal transfer element 9 is enclosed in a pouch 8 with the second fastener 5B, preferably hook material, affixed to one side of the pouch 8. Furthermore, the above steps can be repeated in any order to attach a plurality of thermal transfer elements 9 to a plurality of locations 6 contacting a plurality of body parts 7.

It should be understood that various alternative embodiments, not illustrated herein, are covered by the scope of the appended claims. For example, in one alternative the thermal transfer element can be adjustably secured to the exterior surface of the first layer, inside an outer layer. In this embodiment, the exterior surface of the first layer can be a brushed material suitable for use as loop material in a hook and loop fastener.

In another alternative embodiment of the present invention, the thermal transfer element can be adjustably secured to the interior surface of the first layer, whether or not there is also an outer layer. In this embodiment, the interior surface of the first layer can be a brushed material suitable for use as loop material in a hook and loop fastener.

In other alternative embodiments, the first fastener 5A and the second fastener 5B can be various different types of complementary fasteners other than hook and loop fasteners. For example, the fasteners can be metal or plastic snaps, hooks that engage with rivets, pairs of zipper chains engaged by a zipper, a button and buttonhole, or the like.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An item of clothing sized and dimensioned to fit a human, for use with a thermal transfer element having a footprint of at least 25 cm$^2$, comprising:

inner and outer flexible layers defining a space;

the space having an interior surface that is at least partially covered by a hook or loop material such that the thermal transfer element can be repositionably secured in either of at least first and second non-overlapping positions within the space; and an opening through the outer layer that provides access to the space, and through which the thermal transfer element can be removably inserted into the space.

2. The item of clothing of claim 1, wherein the clothing is selected from the list consisting of a shirt and a jacket.

3. The item of clothing of claim 2, wherein the space extends across an upper back region of the clothing.

4. The item of clothing of claim 1, wherein the clothing comprises a pair of pants.

5. The item of clothing of claim 4, wherein the space extends across a thigh area of the pants.

6. The item of clothing of claim 1, wherein the outer layer includes the interior surface, which is selected from the list consisting of a knitted fabric, a woven fabric, a napped material, and a looped material.

7. The item of clothing of claim 1, wherein the interior surface has an area of at least 200 cm$^2$.

8. The item of clothing of claim 1, wherein the interior surface has an area of at least 600 cm$^2$.

9. The item of clothing of claim 1, wherein the clothing can be adjusted so that the space has a volume of at least 1000 cm$^3$.

10. The item of clothing of claim 1, wherein the clothing can be adjusted so that the space has a volume of at least 8000 cm$^3$.

11. The item of clothing of claim 1, wherein the opening is disposed at a region of the outer layer selected from the list consisting of a shoulder and an upper arm region.

12. The item of clothing of claim 1, wherein the opening is disposed at a region of the outer layer selected from the list consisting of a side torso region of the clothing, and wherein the space extends around front, sides and lower back regions of the clothing.

13. The item of clothing of claim 1, wherein the opening is disposed at a front pocket region of the clothing, and wherein the space extends downward into a lower region of the clothing.

14. The item of clothing of claim 1, further comprising a closure mechanism at the opening.

15. The item of clothing of claim 1, further comprising a second opening that provides access to the space.

16. The item of clothing of claim 1, further comprising a second space having a second interior surface that is at least partially covered by a hook or loop material, and a second opening that provides access to the second space.

17. A combination comprising an item of clothing according to claim 1, and a pouch having (a) an outer surface that cooperates with the hook or loop material of the interior surface, and (b) that includes a cavity into which the thermal transfer element can be received.

18. The combination of claim 17, wherein the pouch includes a closure mechanism.

19. The combination of claim 17, further comprising thermal insulation on a side of the pouch that cooperates with the hook or loop material of the inner surface.

* * * * *